United States Patent [19]

Costantini et al.

[11] Patent Number: 4,565,895

[45] Date of Patent: Jan. 21, 1986

[54] PROCESS FOR THE PREPARATION OF 4-HYDROXY-2,4,6-TRIMETHYL-2,5-CYCLOHEXADIENONE

[75] Inventors: Michel Costantini, Lyons; Francoise Igersheim, Villeurbanne; Léon Krumenacker, Serezin du Rhone, all of France

[73] Assignee: Rhone-Poulenc Sante, Courbevoie, France

[21] Appl. No.: 652,919

[22] Filed: Sep. 21, 1984

[30] Foreign Application Priority Data

Sep. 22, 1983 [FR] France .................................. 83 15071

[51] Int. Cl.$^4$ ............................................. C07C 45/29
[52] U.S. Cl. .................................................. 568/362
[58] Field of Search .......................................... 568/362

[56] References Cited

U.S. PATENT DOCUMENTS

| | | | |
|---|---|---|---|
| 3,928,453 | 12/1975 | Atkinson | 568/362 |
| 4,477,682 | 10/1984 | Tomita et al. | 568/362 |

FOREIGN PATENT DOCUMENTS

| | | | |
|---|---|---|---|
| 1434526 | 12/1966 | France | 568/362 |
| 2258361 | 5/1975 | France | 568/362 |
| 53-438 | 3/1978 | Japan | 568/362 |

OTHER PUBLICATIONS

Ichikawa et al., Chem. Abst., vol. 80, #47544x (1974).
Mitsui, Chem. Abst., vol. 98, #125630k (1983).
Mitsui, Chem. Abst., vol. 99, #121885v (1983).

*Primary Examiner*—James H. Reamer
*Attorney, Agent, or Firm*—Stevens, Davis, Miller & Mosher

[57] ABSTRACT

4-Hydroxy-2,4,6-trimethyl-2,5-cyclohexadienone is prepared by oxidation of 2,4,6-trimethylphenol with a manganese derivative of valency greater than 2 in an aqueous acidic medium.

9 Claims, No Drawings

PROCESS FOR THE PREPARATION OF 4-HYDROXY-2,4,6-TRIMETHYL-2,5-CYCLOHEXADIENONE

The present invention relates to the preparation of 4-hydroxy-2,4,6-trimethyl-2,5-cyclohexadienone, which is an intermediate for the synthesis of trimethylhydroquinone (TMHQ) which is itself a precursor of vitamin E.

It is known that 4-hydroxy-2,4,6-trimethyl-2,5-cyclohexadienone can be prepared by oxidation of 2,4,6-trimethylphenol, for example with a peracid or molecular oxygen in a basic medium. However, oxidation with air under a pressure in the region of 100 bars poses difficulties in its technical accomplishment, linked to significant safety problems.

4-Hydroxy-2,4,6-trimethyl-2,5-cyclohexadienone can be converted into trimethylhydroquinone under the conditions described in French Pat. No. 73/33374, published under No. 2,200,225, i.e. by heating at a temperature of at least 100° C. in a non-acidic liquid medium such as methanol in aqueous medium.

It is also known from French Pat. No. 70/23875, published under No. 2,051,407, that trimethylhydroquinone can be prepared by sulphonation of 2,3,6-trimethylphenol, and oxidation of the 2,3,6-trimethylphenol-4-sulphonic acid formed followed by immediate reduction of the resulting trimethylquinone. Sulphonation is generally performed with concentrated sulphuric acid at a temperature below or equal to 60° C. The oxidation is carried out with an oxidising agent chosen from chromic acid, manganese dioxide or manganic sulphate at a temperature below or equal to the boiling point of the reaction mixture. The reduction is preferably carried out with sodium dithionite.

It has now been found, and this is the subject of the present invention, that 4-hydroxy-2,4,6-trimethyl-2,5-cyclohexadienone can be obtained by oxidation of 2,4,6-trimethylphenol with a manganese derivative of valency greater than 2 in an aqueous acidic medium.

The manganese derivative of valency greater than 2 may be, for example, manganese dioxide, potassium permanganate or manganic sulphate, or a mixture of these. It is particularly advantageous to use manganese dioxide as the oxidising agent.

The oxidation reaction is generally carried out in the presence of a strong acid such as sulphuric acid, perchloric acid or a sulphonic acid e.g. methanesulphonic acid, or p-toluenesulphonic acid. It is particularly advantageous to work in an aqueous phase having a pH between $-1$ and $+1$ and preferably between $-0.8$ and $+0.5$.

The process of the invention can be carried out by adding the manganese derivative to 2,4,6-trimethylphenol suspended in an aqueous acidic medium or in solution in an organic solvent in contact with the aqueous acidic medium. The manganese derivative can be added in solid form or in the form of a suspension or aqueous solution.

The process can also be carried out by adding 2,4,6-trimethylphenol, optionally in solution in an organic solvent, to a suspension or solution of the manganese derivative in an aqueous acidic medium optionally containing an organic solvent.

When the process is carried out in the presence of an organic solvent, the latter may be, for example, an aromatic hydrocarbon (e.g. benzene), an aliphatic (e.g. hexane) or cycloaliphatic (e.g. cyclohexane) hydrocarbon, an ether (e.g. diisopropyl ether), an ester (e.g. ethyl acetate), a chlorinated solvent (e.g. carbon tetrachloride or methylene chloride) or an organic acid (e.g. acetic acid).

When manganese dioxide is used as the oxidising agent, it is particularly advantageous to use a molecular ratio of manganese dioxide to 2,4,6-trimethylphenol of between 1 and 2, and preferably in the region of 1.5.

The process is generally carried out at a temperature between $-10°$ C. and the boiling point of the reaction mixture, and preferably between $-10°$ and 30° C.

The process can also be carried out by gradually adding the strong acid to a mixture of the manganese derivative and 2,4,6-trimethylphenol in water acidified to a pH in the region of $-0.6$, optionally in the presence of an organic solvent so as to maintain the pH in the region of $-0.6$.

When the procedure is performed in the absence of an organic solvent, the 4-hydroxy-2,4,6-trimethyl-2,5-cyclohexadienone can be isolated after extraction of the reaction mixture by an organic solvent immiscible with water.

When the procedure is performed in the presence of an organic solvent, the 4-hydroxy-2,4,6-trimethyl-2,5-cyclohexadienone can be isolated after decantation and then extraction of the aqueous phase by an organic solvent immiscible with water.

In either case, the 4-hydroxy-2,4,6-trimethyl-2,5-cyclohexadienone is obtained in solution in the organic solvent, which only needs to be evaporated for the product to be isolated.

It is possible to purify 4-hydroxy-2,4,6-trimethyl-2,5-cyclohexadienone from its solution in an organic solvent after washing the latter with water and then extracting the aqueous phase with an organic solvent immiscible with water. The 4-hydroxy-2,4,6-trimethyl-2,5-cyclohexadienone is isolated after evaporation of the solvent, and optionally after distillation.

The process of the present invention provides a degree of conversion of 2,4,6-trimethylphenol in the region of 100%, and the yield of 4-hydroxy-2,4,6-trimethyl-2,5-cyclohexadienone is generally between 65 and 70%.

The examples which follow show how the invention can be put into practice.

EXAMPLE 1

In a 500 cc round-bottomed flask, equipped with central stirring, a dropping funnel, a reflux condenser and a thermometer, there are introduced manganese dioxide (3.9 g; 37.1 mmol), water (170 cc) and concentrated sulphuric acid (d=1.83; 30 g). The mixture is cooled to a temperature in the region of 0° C. Isopropyl ether (100 cc) is added. There is then added, in the course of 30 minutes, 2,4,6-trimethylphenol (3.4 g; 25 mmol) dissolved in isopropyl ether (60 cc). The dropping funnel is rinsed with isopropyl ether (25 cc). After 5 hours 30 minutes of stirring at a temperature between 0° and 5° C., the reaction mixture is decanted. The aqueous phase is extracted with isopropyl ether (3×25 cc). In the combined organic phases, the following are determined by gas chromatography: 2,4,6-trimethylphenol (0.65 mmol) and 4-hydroxy-2,4,6-trimethyl-2,5-cyclohexadienone (16 mmol).

The degree of conversion of 2,4,6-trimethylphenol is 97.4% and the yield of 4-hydroxy-2,4,6-trimethyl-2,5- cyclohexadienone is 65.7% relative to the 2,4,6-trimethylphenol converted.

EXAMPLE 2

The procedure is as in Example 1, but replacing isopropyl ether by the same volumes of carbon tetrachloride. Three hours after the end of the addition of the 2,4,6-trimethylphenol, the reaction mixture is decanted and the aqueous phase is extracted with isopropyl ether (3×25 cc). In the combined organic phases, the following are determined by gas chromatography: 2,4,6-trimethylphenol (0.5 mmol) and 4-hydroxy-2,4,6-trimethyl-2,5-cyclohexadienone (16.8 mmol).

The degree of conversion of 2,4,6-trimethylphenol is 98% and the yield of 4-hydroxy-2,4,6-trimethyl-2,5-cyclohexadienone is 68.7% relative to the 2,4,6-trimethylphenol converted.

EXAMPLE 3

In an apparatus similar to that described in Example 1, but using a 2 liter round-bottomed flask, there are introduced manganese dioxide (15.74 g; 150 mmol), water (680 cc) and concentrated sulphuric acid (d=1.83; 120 g). The mixture is cooled to 0° C. and then carbon tetrachloride (100 cc) is added. There is then added, in the course of 45 minutes, 2,4,6-trimethylphenol (13.6 g; 100 mmol) dissolved in carbon tetrachloride (80 cc). The dropping funnel is rinsed with carbon tetrachloride (20 cc).

After 4 hours of stirring at a temperature between 0° and 5° C., the reaction mixture is decanted and the aqueous phase is extracted with isopropyl ether (6×100 cc). In the combined organic phases, the following are determined by gas chromatography: 2,4,6-trimethylphenol (3.9 mmol) and 4-hydroxy-2,4,6-trimethyl-2,5-cyclohexadienone (66.4 mmol).

The degree of conversion of 2,4,6-trimethylphenol is 95.9% and the yield of 4-hydroxy-2,4,6-trimethyl-2,5-cyclohexadienone is 69.1% relative to the 2,4,6-trimethylphenol converted.

EXAMPLE 4

In a 250 cc round-bottomed flask equipped with central stirring, a dropping funnel, a reflux condenser and a thermometer, there are introduced manganese dioxide (3.96 g; 37.7 mmol), water (44.5 cc) and concentrated sulphuric acid (d=1.82; 10 g). The mixture is cooled to the region of 0° C. and carbon tetrachloride (20 cc) is then added. There is then added, in the course of 16 minutes, 2,4,6-trimethylphenol (3.4 g; 25 mmol) dissolved in carbon tetrachloride (25 cc). The dropping funnel is rinsed with carbon tetrachloride (5 cc). After 4 hours 10 minutes of stirring at a temperature between 0° and 5° C., the reaction mixture is decanted and the aqueous layer is extracted with carbon tetrachloride (3×25 cc). In the combined organic phases, the following are determined by gas chromatography: 2,4,6-trimethylphenol (1.3 mmol) and 4-hydroxy-2,4,6-trimethyl-2,5-cyclohexadienone (10.8 mmol).

The degree of conversion of 2,4,6-trimethylphenol is 94.8% and the yield of 4-hydroxy-2,4,6-trimethyl-2,5-cyclohexadienone is 45.6% relative to the 2,4,6-trimethylphenol converted.

EXAMPLE 5

In the apparatus described in Example 1, there are introduced manganese dioxide (2.6 g; 25 mmol), water (170 cc) and concentrated sulphuric acid (d=1.83; 30 g). The mixture is cooled to 0° C. and then isopropyl ether (100 cc) is added. There is then added, in the course of 20 minutes, 2,4,6-trimethylphenol (3.4 g; 25 mmol) dissolved in isopropyl ether (60 cc). The dropping funnel is rinsed with isopropyl ether (25 cc). After 4 hours 30 minutes of stirring at a temperature between 0° and 5° C., the reaction mixture is decanted and the aqueous layer is extracted with isopropyl ether (3×20 cc). In the combined organic phases, the following are determined by gas chromatography: 2,4,6-trimethylphenol (9.1 mmol) and 4-hydroxy-2,4,6-trimethyl-2,5-cyclohexadienone (9.2 mmol).

The degree of conversion of 2,4,6-trimethylphenol is 63.6% and the yield of 4-hydroxy-2,4,6-trimethyl-2,5-cyclohexadienone is 58.1% relative to the 2,4,6-trimethylphenol converted.

EXAMPLE 6

In the apparatus described in Example 1, there are introduced water (170 cc), concentrated sulphuric acid (d=1.83; 30 g), isopropyl ether (160 cc) and 2,4,6-trimethylphenol (3.4 g; 25 mmol). The mixture is cooled to 0° C. and then manganese dioxide (2.6 g; 25 mmol) is added in the course of 4 hours 30 minutes. After 2 hours of stirring after the end of the addition, the reaction mixture is decanted and the aqueous layer is extracted with isopropyl ether (3×25 cc). In the combined organic phases, the following are determined by gas chromatography: 2,4,6-trimethylphenol (9.9 mmol) and 4-hydroxy-2,4,6-trimethyl-2,5-cyclohexadienone (6.8 mmol).

The degree of conversion of 2,4,6-trimethylphenol is 65.6% and the yield of 4-hydroxy-2,4,6-trimethyl-2,5-cyclohexadienone is 45% relative to the 2,4,6-trimethylphenol converted.

EXAMPLE 7

In the apparatus described in Example 1, there are introduced manganese dioxide (2.62 g; 25 mmol), water (170 cc) and concentrated sulphuric acid (d=1.83; 30 g). The mixture is cooled to 0° C. and there is then added, in the course of 20 minutes, 2,4,6-trimethylphenol (3.4 g) dissolved in acetic acid (10 cc). After 2 hours 30 minutes of stirring at a temperature between 0° and 5° C., isopropyl ether (50 cc) is added.

The mixture is extracted with isopropyl ether (4×30 cc). The organic phases are combined and then washed with water (20 cc). In the organic phases, there are determined by gas chromatography: 2,4,6-trimethylphenol (8.9 mmol) and 4-hydroxy-2,4,6-trimethyl-2,5-cyclohexadienone (5.9 mmol).

The degree of conversion of 2,4,6-trimethylphenol is 64.4% and the yield of 4-hydroxy-2,4,6-trimethyl-2,5-cyclohexadienone is 36.6% relative to the 2,4,6-trimethylphenol converted.

EXAMPLE 8

In an apparatus identical to that described in Example 4, there are introduced water (184 cc), 100% strength sulphuric acid (d=1.83; 3.4 g), manganese dioxide (3.9 g; 37.5 mmol) and carbon tetrachloride (20 cc). The mixture is cooled to 0° C. and 2,4,6-trimethylphenol (3.45 g; 25 mmol) in carbon tetrachloride (50 cc) is then added rapidly. The reaction mixture is stirred for 4 hours at a temperature between 0° and 5° C. After filtering and decantation, the aqueous layer is extracted with carbon tetrachloride.

In the combined organic phases there are determined:

2,4,6-trimethylphenol (4.7 mmol) and
4-hydroxy-2,4,6-trimethyl-2,5-cyclohexadienone (7.7 mmol).

The degree of conversion of 2,4,6-trimethylphenol is 81% and the yield of 4-hydroxy-2,4,6-trimethyl-2,5-cyclohexadienone, relative to the 2,4,6-trimethylphenol which has reacted, is 38%.

EXAMPLE 9

In an apparatus identical to that described in Example 4, but using a 1 liter round-bottomed flask, there are introduced manganese dioxide (3.96 g), 70% strength perchloric acid (87 g), water (143 g) and carbon tetrachloride (187 g). The mixture is cooled to 0° C. and 2,4,6-trimethylphenol (3.45 g) dissolved in carbon tetrachloride (50 cc) is then added. The reaction mixture is stirred for 4 hours at between 0° and 5° C. After the customary treatment, analysis of the organic phases shows that the degree of conversion of 2,4,6-trimethylphenol is 81% and the yield of 4-hydroxy-2,4,6-trimethyl-2,5-cyclohexadienone, relative to the 2,4,6-trimethylphenol which has reacted, is 20%.

EXAMPLE 10

In a 500 cc round-bottomed flask equipped with central stirring, a reflux condenser and a thermometer, there are introduced manganese dioxide (3.9 g), 100% strength sulphuric acid (d=1.83; 30 g), water (170 cc) and 2,4,6-trimethylphenol (3.4 g). The reaction mixture is stirred for 3 hours 50 minutes at a temperature between 0° and 5° C. and is then extracted with methylene chloride (4×50 cc). Analysis of the combined organic phases shows that the degree of conversion of 2,4,6-trimethylphenol is 93% and the yield of 4-hydroxy-2,4,6-trimethyl-2,5-cyclohexadienone, relative to the 2,4,6-trimethylphenol converted, is 62%.

EXAMPLE 11

In a 500 cc round-bottomed flask equipped with central stirring, a reflux condenser and a thermometer, there are introduced manganese dioxide (3.9 g), methane-sulphonic acid (59.4 g), water (186 cc) and methylene chloride (20 cc). This mixture is cooled to 0° C. and a solution of 2,4,6-trimethylphenol (3.4 g) in methylene chloride (30 cc) is then rapidly added. The reaction mixture is stirred for 1 hour at between 0° and 5° C.

After decantation, and extraction of the aqueous phase with methylene chloride (4×50 cc), analysis of the combined organic phases shows that the degree of conversion of 2,4,6-trimethylphenol is 93% and the yield of 4-hydroxy-2,4,6-trimethyl-2,5-cyclohexadienone, relative to the 2,4,6-trimethylphenol which has reacted, is 50%.

EXAMPLE 12

In an apparatus identical to that described in Example 1, there are introduced manganese sulphate monohydrate (6.76 g), water (170 cc), 100% strength sulphuric acid (d=1.83; 30 g) and potassium permanganate (1.58 g). To the reaction mixture cooled to 0° C., there is rapidly added 2,4,6-trimethylphenol (3.42 g) dissolved in methylene chloride (50 cc). The reaction mixture is stirred for 2 hours 40 minutes at 0° C. After the customary treatment, analysis of the combined organic phases shows that the degree of conversion of 2,4,6-trimethylphenol is 61% and the yield of 4-hydroxy-2,4,6-trimethyl-2,5-cyclohexadienone, relative to the 2,4,6-trimethylphenol which has reacted, in 20%.

EXAMPLE 13

In an apparatus identical to that described in Example 1, there are introduced water (170 cc), concentrated sulphuric acid (d=1.83; 30 g), manganese dioxide (3.9 g; 37.1 mmol) and methylene chloride (20 cc). There is then added, in the course of 10 minutes, 2,4,6-trimethylphenol (3.4 g) dissolved in methylene chloride (20 cc). The mixture is maintained at 25° C. for 1 hour 20 minutes. The reaction mixture is then decanted and the aqueous phase is extracted with methylene chloride (3×50 cc). In the combined organic phases the following are determined by gas chromatography:

2,4,6-trimethylphenol (4.3 mmol)
4-hydroxy-2,4,6-trimethyl-2,5-cyclohexadienone (14.1 mmol).

The degree of conversion of 2,4,6-trimethylphenol is 82.8%.

The yield of 4-hydroxy-2,4,6-trimethyl-2,5-cyclohexadienone is 68.1% relative to the 2,4,6-trimethylphenol converted.

EXAMPLE 14

In an apparatus identical to that described in Example 1, there are introduced water (89 cc), concentrated sulphuric acid (d=1.83; 19 g) and manganese dioxide (7.9 g). The mixture is cooled to a temperature in the region of 0° C. There is then added, in the course of approximately 2 minutes, 2,4,6-trimethylphenol (6.8 g) dissolved in methylene chloride (100 cc). There is then added, in the course of 15 minutes, concentrated sulphuric acid (3.9 g) and then, in the course of 75 minutes, concentrated sulphuric acid (3.9 g). The stirring is continued for a further 30 minutes. The reaction mixture is then decanted and the aqueous phase is extracted with methylene chloride (4×50 cc). In the combined organic phases, the following are determined by gas chromatography:

2,4,6-trimethylphenol (0.4 mmol)
4-hydroxy-2,4,6-trimethyl-2,5-cyclohexadienone (36.5 mmol).

The degree of conversion of mesitol is 99.2%.

The yield of 4-hydroxy-2,4,6-trimethyl-2,5-cyclohexadienone is 73.4% relative to 2,4,6-trimethylphenol converted.

We claim:

1. A process for the preparation of 4-hydroxy-2,4,6-trimethyl-2,5-cyclohexadienone, which comprises oxidising 2,4,6-trimethylphenol with a manganese derivative of valency greater than 2 in an aqueous acidic medium, and isolating the product obtained.

2. A process according to claim 1, in which the manganese derivative is a member selected from the class consisting of manganese dioxide, potassium permanganate, manganic sulphate, and mixtures of these.

3. A process according to claim 1, in which the aqueous acidic medium comprises sulphuric acid, perchloric acid or a sulphonic acid.

4. A process according to claim 1, in which the pH of the aqueous phase is from −0.8 to +0.5.

5. A process according to claim 1, in which the oxidation is carried out in the presence of an organic solvent.

6. A process according to claim 5 in which the said organic solvent is an aromatic aliphatic or cycloaliphatic hydrocarbon, an ether, an ester, a chlorinated solvent or an aliphatic organic acid.

7. A process according to claim 1, in which the oxidation is performed at a temperature from −10° C. to the boiling point of the reaction mixture.

8. A process according to claim 2, in which manganese dioxide is used and the mole ratio of manganese dioxide to 2,4,6-trimethylphenol is 1 to 2.

9. A process according to claim 1, in which 2,4,6-trimethylphenol is oxidized with manganese dioxide in an aqueous sulphuric acid medium at a pH between −1 and +1 and in the presence of an inert organic solvent at a temperature from −10° C. to +30° C., the molecular ratio of manganese dioxide to 2,4,6-trimethylphenol being from 1 to 2.

* * * * *